(12) United States Patent
Qian et al.

(10) Patent No.: US 7,361,512 B2
(45) Date of Patent: Apr. 22, 2008

(54) LOW HEMOGLOBIN CONCENTRATION CELL PERCENTAGE AND METHOD OF USE IN DETECTION OF IRON DEFICIENCY

(75) Inventors: Cheng Qian, Miami, FL (US); Ziling Huo, Miami, FL (US); Ramon Simon-Lopez, St. Cergue (CH)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 11/624,845

(22) Filed: Jan. 19, 2007

(65) Prior Publication Data

US 2007/0172955 A1    Jul. 26, 2007

Related U.S. Application Data

(60) Provisional application No. 60/760,520, filed on Jan. 20, 2006.

(51) Int. Cl.
*G01N 33/72* (2006.01)
*G01N 33/48* (2006.01)

(52) U.S. Cl. .......................... 436/66; 436/10; 436/63; 436/84; 435/2

(58) Field of Classification Search ............... 436/8, 436/10, 63, 66, 84; 435/2; 530/385
See application file for complete search history.

(56) References Cited

U.S. PATENT DOCUMENTS

| | | | |
|---|---|---|---|
| 2,656,508 A | | 10/1953 | Coulter |
| 3,810,011 A | | 5/1974 | Coulter et al. |
| 4,030,888 A | * | 6/1977 | Yamamoto et al. ........... 422/67 |
| 4,521,518 A | | 6/1985 | Carter et al. |
| 4,528,274 A | | 7/1985 | Carter et al. |
| 5,125,737 A | | 6/1992 | Rodriguez et al. |
| 5,763,280 A | | 6/1998 | Li et al. |
| 5,834,315 A | | 11/1998 | Riesgo et al. |
| 5,882,934 A | | 3/1999 | Li et al. |
| 5,935,857 A | | 8/1999 | Riesgo et al. |
| 6,030,838 A | * | 2/2000 | Telmissani .................... 436/63 |
| 6,228,652 B1 | * | 5/2001 | Rodriguez et al. ............ 436/63 |
| 6,268,217 B1 | * | 7/2001 | Barton et al. ................. 436/66 |
| 6,573,102 B2 | | 6/2003 | Li et al. |
| 6,706,526 B2 | | 3/2004 | Lang et al. |
| 6,916,662 B2 | * | 7/2005 | Kendall et al. ............... 436/70 |
| 2003/0027347 A1 | | 2/2003 | Shapiro |
| 2004/0241769 A1 | | 12/2004 | Crews et al. |
| 2007/0072170 A1 | * | 3/2007 | Simon-Lopez ................. 435/4 |
| 2007/0072300 A1 | * | 3/2007 | Simon-Lopez ............... 436/43 |
| 2007/0172956 A1 | * | 7/2007 | Magari et al. ................ 436/66 |

FOREIGN PATENT DOCUMENTS

JP         11-326315      * 11/1999

OTHER PUBLICATIONS

Bain, B.J., Blood Cells, A Practical Guide, Second Edition, Blackwell Science Ltd., 1995, Chapter 8, pp. 197-199.
Eknoyan, G., et al, "Continuous quality improvement: DOQI becomes K/DOQI and is updated". Am J Kidney Dis., Jan. 2001; 37(1): 179-194.
Eschbach, J., "Anemia Management in Chronic Kidney Disease: Role of Factors Affecting Epoetin Responsiveness". J. Am Soc Nephrol 13: 1412-1414, 2002.
Thomas, et al, "Biochemical Markers and Hematologic Indices in the Diagnosis of Functional Iron Deficiency", Clin Chem 48:7, 1066-1076, 2002.
Machin, S.J., et al, "Functional Iron Deficiency and New Red Cell Parameters on the Sysmex XE-2100", ISLH XIVth Int'l Symposium, 2001.
Thomas, C., et al, "Anemia of Chronic Disease: Pathophysiology and Laboratory Diagnosis", Lab Hematology, vol. 11, pp. 14-23, 2005.
Locatelli, et al, "Revised European Best Practice Guidelines for the Management of Anaemia in Patients with Chronic Renal Failure", Nephrology and Dialysis Transplantation, vol. 19 Supp 2, May 2004 pp. ii22-24 and ii39-41.

* cited by examiner

*Primary Examiner*—Maureen M. Wallenhorst
(74) *Attorney, Agent, or Firm*—Cuspa Technology Law Associates; Mitchell E. Alter

(57) ABSTRACT

A method of producing low hemoglobin concentration cell percentage (LHCC %) and the method of use for detection of iron deficiency have been disclosed. LHCC % is a sigmoid function of mean cell hemoglobin concentration (MCHC), which correlates linearly with hypochromic red cell percentage.

13 Claims, 5 Drawing Sheets

LOW HEMOGLOBIN CONCENTRATION CELL PERCENTAGE AND METHOD OF USE IN DETECTION OF IRON DEFICIENCY

CROSS REFERENCE TO RELATED APPLICATION

This application claims the benefit under 35 USC 119 (e) of the provisional patent application Ser. No. 60/760,520, filed on Jan. 20, 2006, which is hereby incorporated by reference in its entirety.

FIELD OF THE INVENTION

The present invention relates to a method of producing a new diagnostic parameter, low hemoglobin concentration cell percentage, and the method of use in detection of iron deficiency.

BACKGROUND OF THE INVENTION

Iron deficiency (ID) is the most prevalent single deficiency state on a worldwide basis. It is important economically because it diminishes the capability of individuals who are affected to perform physical labor, and it diminishes both growth and learning in children.

Absolute iron deficiency, with anemia or without anemia, and functional iron deficiency (FID) are high frequency clinical conditions, and these patients have iron deficient erythropoiesis. Absolute iron deficiency is defined as a decreased total iron body content. Iron deficiency anemia (IDA) occurs when iron deficiency is sufficiently severe to diminish erythropoiesis and cause the development of anemia. Functional iron deficiency describes a state where the total iron content of the body is normal or even elevated, but the iron is 'locked away' and unavailable for the production of red blood cells. This condition is observed mainly in patients with chronic renal failure who are on hemodialysis, and in patients with chronic inflammation or chronic infections.

Iron status can be measured using hematological and biochemical indices. Each parameter of iron status reflects changes in different body iron compartments and is affected at different levels of iron depletion. Specific iron measurements include hemoglobin (Hgb), mean cell volume (MCV), hematocrit (Hct), erythrocyte protoporphyrin, plasma iron, transferrin, transferrin saturation levels (TSAT), serum ferritin (SF) and more recently soluble transferrin receptors (sTfR) and red-cell distribution width (RDW).

Typical values for normal iron status are SF 100±60 ng/mL and Hgb 12-17 g/dL for women and 14-19 g/dL for men. The typical values for iron deficiency anemia are SF <22 ng/mL, Hgb for women <12 g/dL and for men <13 g/dL.

Hemoglobin (Hgb) has been used longer than any other iron status parameter. It provides a quantitative measure of the severity of iron deficiency once anemia has developed. Hemoglobin determination is a convenient and simple screening method and is especially useful when the prevalence of iron deficiency is high, as in pregnancy or infancy. The limitations of using hemoglobin as a measure of iron status are its lack of specificity (as factors such as vitamin $B_{12}$ or folate deficiency, genetic disorders and chronic infections can limit erythropoiesis) and its relative insensitivity due to the marked overlap in values between normal and iron deficient populations. To identify iron deficiency anemia, hemoglobin is measured together with more selective measurements of iron status.

A reduction in mean cell volume (MCV) occurs when iron deficiency becomes severe, at about the same time as anemia starts to develop. It is a fairly specific indicator of iron deficiency once thalassemia and the anemia of chronic disease have been excluded. A cut-off value of 80 fl is accepted as the lower limit of normal in adults. It has been reported that when measured on Technicon hematology analyzers (that use optical measurement of red blood cells) iron deficiency blood samples have reduced mean cell hemoglobin (MCH), and mean cell hemoglobin concentration (MCHC). However, when measured by impedance-based hematology analyzers (Such as Coulter or Sysmex instruments) MCHC is insensitive but more specific for iron deficiency (Bain, B. J., Blood Cells, A Practical Guide, Second Edition, Blackwell Science Ltd., 1995, Chapter 8, pages 197-199). The red-cell distribution width (RDW) has been used recently in combination with other parameters for the classification of anemias. It reflects the variation in the size of the red cells and can be used to detect subtle degrees of anisocytosis.

The most commonly used iron status parameters at present are transferrin saturation (TSAT) and serum ferritin (SF). However, both are indirect measures of iron status. Transferrin is a transport protein that contains two iron binding sites by which it transports iron from storage sites to erythroid precursors. TSAT (i.e., the percentage of total binding sites that are occupied by iron) is a measure of iron that is available for erythropoiesis. TSAT is calculated by dividing the serum iron by the total iron binding capacity (TIBC), a measurement of circulating transferrin, and multiplying by 100. Ferritin is a storage protein that is contained primarily within the reticuloendothelial system, with some amounts released in the serum. Under conditions of iron excess, ferritin production increases to offset the increase in plasma iron. The level of ferritin in the serum, therefore, reflects the amount of iron in storage.

| Definition of Functional Iron Deficiency (FID) and Absolute Iron Deficiency (AID) by Kidney Disease Outcomes, Quality Initiative K/DOQI (U.S.A) | | |
|---|---|---|
| Ferritin µg/L | <100 | 100–800 |
| TSAT <20% | AID | |
| TSAT <20% | | FID |

For patients with chronic kidney disease, absolute iron deficiency may be diagnosed when TSAT is <20% and SF is <100 ng/ml. Functional iron deficiency may be more difficult to diagnose since iron status parameters may indicate adequate iron stores. There are different criteria in defining FID, one of them is published by the Kidney Disease Outcomes Quality Initiative—K/DOQI (Eknoyan G, et al. Continuous quality improvement: DOQI becomes K/DOQI and is updated. National Kidney Foundation's Dialysis Outcomes Quality Initiative. *Am J Kidney Dis.*, 2001 January;37(1):179-194; Anemia Management in Chronic Kidney Disease: Role of Factors Affecting Epoetin Responsiveness, ESCHBACH, J., *J Am Soc Nephrol* 13: 1412-1414, 2002.), as shown in the table above.

The limitations of using transferrin saturation reflect those of serum iron, i.e., wide diurnal variation and low specificity. TSAT is also reduced in inflammatory disease. Transferrin saturation is commonly used in population studies combined with other indicators of iron status. On the other hand, as ferritin is an acute phase reactant, its serum levels may be elevated in the presence of chronic inflammation, infection, malignancy and liver disease. Alcohol consumption has also been suggested to independently raise serum ferritin.

Recently, several new red blood cell and reticulocyte parameters have been reported having utilities in detection of iron deficiency and functional iron deficiency. Two of the parameters are hypochromic red cell percentage (referred to as % Hypo) and CHr (reticulocyte hemoglobin content) reported by the Bayer ADVIA 120 hematology analyzer (Thomas et al., Biochemical Markers and Hematologic Indices in the Diagnosis of Functional Iron Deficiency, *Clinical Chemistry* 48:7, 1066-1076, 2002). Hypochromic red cell percentage is defined as the percentage of red blood cells having hemoglobin concentration less than 28 g/dL.

Reticulocytes are immature red blood cells with a life span of only 1 to 2 days. When these are first released from the bone marrow, measurement of their hemoglobin content can provide the amount of iron immediately available for erythropoiesis. A less than normal hemoglobin content in these reticulocytes is an indication of inadequate iron supply relative to demand. The amount of hemoglobin in these reticulocytes also corresponds to the amount of hemoglobin in mature red blood cells. CHr has been evaluated recently in numerous studies as a test for iron deficiency and functional iron deficiency and has been found to be highly sensitive and specific. However, exact threshold values have not been established, as the threshold values vary depending on the laboratory and instrument used.

Erythropoietin is effective in stimulating production of red blood cells, but without an adequate iron supply to bind to hemoglobin, the red blood cells will be hypochromic, i.e., low in hemoglobin content. Thus, in states of iron deficiency, a significant percentage of red blood cells leaving the bone marrow will have a low hemoglobin content. By measuring the percentage of red blood cells with hemoglobin content <28 g/dL, iron deficiency can be detected. % Hypo >10% has been correlated with iron deficiency, and hence has been used as a diagnostic criterion for detection of iron deficiency (Revised European Best Practice Guidelines for the Management of Anaemia in Patients With Chronic Renal Failure, Locatelli, F. et al., *Nephrology and Dyalisis Transplantation*, Volume 19 May 2004 (Supplement 2), Guideline III.2, page ii22-24).

% Hypo is a reported parameter on several Bayer hematology analyzers based on an optical cell-by-cell hemoglobin measurement. % Hypo must be measured using a fresh whole blood sample (less than four hours after blood collection), since storage or sample aging leads to erroneous increases of % Hypo report due to red blood cell swelling (Revised European Best Practice Guidelines for the Management of Anaemia in Patients With Chronic Renal Failure, Locatelli, F. et al., *Nephrology and Dyalisis Transplantation*, Volume 19 May 2004 (Supplement 2), Appendix B, page ii39-41).

Two other parameters have been reported recently correlating to % Hypo and CHr are RBC—Y and Ret-$H_e$ reported by the Sysmex XE-2100 hematology analyzer (Machin S. J. et al. Functional Iron Deficiency and New Red Cell Parameters on the Sysmex XE-2100, ISLH 2001 Industry-Sponsored Workshops, ISLH XIVth International Symposium, 2001; and Thomas, C. et al., Anemia of Chronic Disease: Pathophysiology and Laboratory Diagnosis, *Laboratory Hematology* 2005, 11:14-23). RBC—Y is the mean value of the forward light scatter histogram within the mature erythrocyte population, and Ret-$H_e$ is the mean value of the forward light scatter histogram within the reticulocyte population obtained in a reticulocyte measurement on the Sysmex XE-2100 hematology analyzer.

Most recently, several functions of red blood cell parameters as well as reticulocyte parameters have been disclosed by Simon-Lopez in the co-pending application Ser. No. 11/524,682 to be useful in detection of iron deficiency. These include a RBC size function (RSf) defined as a product function of MCV and MRV, a volume-hemoglobin factor (VHf) defined as a product function of MCV and Hgb, a volume-hemoglobin/distribution factor (VHDWf) defined as a function of MCV, Hgb and RDW.

It has been recognized that CHr and % Hypo are only provided on Bayer's hematology analyzers. Therefore, this information is not available for many clinical laboratories and hospitals. A need exists for developing new diagnostic indicators for detection iron deficiency with comparable clinical accuracy, sensitivity and specificity to the known parameters such as CHr and % Hypo.

SUMMARY OF THE INVENTION

In one embodiment, the present invention is directed to a method of producing low hemoglobin concentration cell percentage (LHCC %) on a hematology analyzer. The method comprises mixing a first aliquot of a blood sample with a blood diluent to form a first sample mixture, analyzing the first sample mixture on the hematology analyzer, and obtaining a mean cell volume of red blood cells (MCV) and a red blood cell concentration (RBC); mixing a second aliquot of the blood sample with a reagent system to form a second sample mixture, analyzing the second sample mixture on the hematology analyzer, and obtaining a hemoglobin concentration (Hgb) of the blood sample; obtaining mean cell hemoglobin concentration (MCHC) using the obtained MCV, RBC and Hgb; obtaining a low hemoglobin concentration cell percentage (LHCC %) using the obtained MCHC; and reporting the LHCC % of the blood sample on the hematology analyzer.

In one embodiment, LHCC % is a sigmoid function defined by the equation of LHCC %=1/(1+(EXP(d*(q−MCHC))))*100, wherein d and q are constants. In one exemplary embodiment, d and q are 1.8 and 30, respectively. In another embodiment, an enhanced LHCC % is provided, which is defined by the equation of Enhanced LHCC %=SQRT((1−(1/(1+(EXP(d*(q−MCHC))))))*100, wherein d and q are constants.

In a further embodiment, the present invention is directed to a method of detection of iron deficiency using LHCC %, or the enhanced LHCC %, both of which have a similar diagnostic ability as % Hypo in detection of iron deficiency. In one embodiment, the method comprises the steps of analyzing a blood sample on a hematology analyzer and obtaining MCHC of the red blood cells; obtaining LHCC % defined as a sigmoid function of the MCHC; comparing the LHCC % to a predetermined LHCC % iron deficiency criterion; and reporting an indication of iron deficiency if the LHCC % meets the predetermined LHCC % iron deficiency criterion.

The advantages of the present invention will become apparent from the following description taken in conjunction with the accompanying drawings showing exemplary embodiments of the invention.

DETAILED DESCRIPTION OF THE INVENTION

Figure 1A:
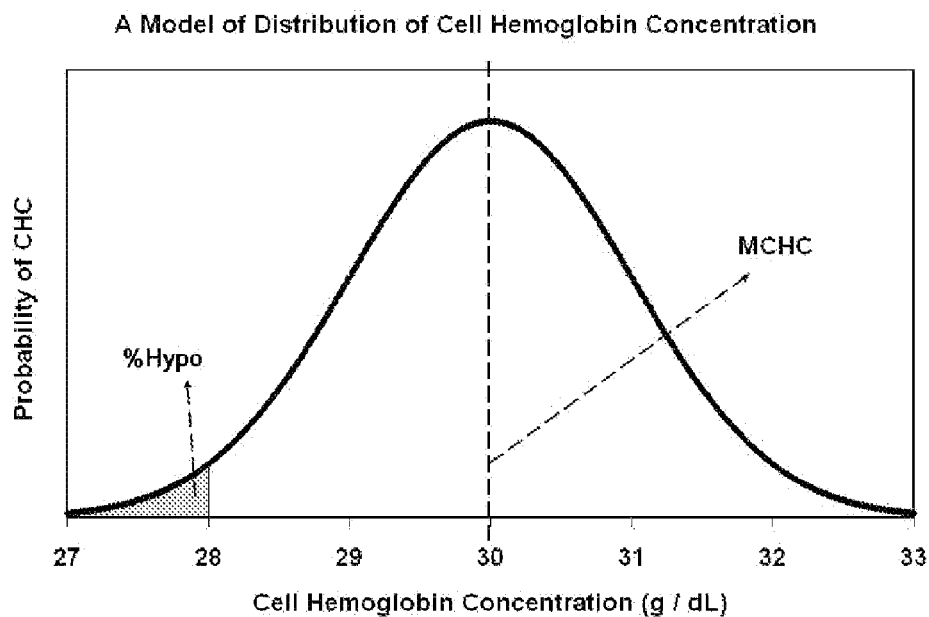
FIG. 1A is a graphic illustration of red blood cell distribution and the distribution of hypochromic red blood cells.

The present invention provides a new diagnostic parameter, low hemoglobin concentration cell percentage (LHCC %) and the method of use for detection of iron deficiency.

The term of iron deficiency used herein includes absolute iron deficiency and functional iron deficiency (FID). Absolute iron deficiency, frequently referred to as iron deficiency in the literature, is defined as a decreased total iron body content. Iron deficiency anemia (IDA) occurs when iron deficiency is sufficiently severe to diminish erythropoiesis and cause the development of anemia. Latent iron deficiency refers to the presence of iron deficiency but not yet anemia. On the other hand, functional iron deficiency defines a state where the total iron content of the body is normal or even elevated, but the iron is unavailable for the production of red blood cells. This condition is observed mainly in patients with chronic renal failure who are on hemodialysis. Latent functional iron deficiency refers to the pre-anemic stage of functional Iron deficiency. Individuals having different forms of iron deficiency, as described above, have different extents of iron deficient erythropoiesis.

In one aspect, the present invention provides a method of producing the low hemoglobin concentration cell percentage (LHCC %) of a blood sample on a hematology analyzer.

In one embodiment, the low hemoglobin concentration cell percentage (LHCC %) is a sigmoid function of mean cell hemoglobin concentration (MCHC), defined by the following equation:

$$LHCC \% = 1/(1+(EXP(d*(q-MCHC))))*100$$

wherein d and q are constants. In one exemplary embodiment, d and q are 1.8 and 30, respectively.

Mean cell hemoglobin concentration (MCHC), also referred to as hemoglobin concentration per red blood cell, is defined by the equation of MCHC=(Hgb/(RBC*MCV))*1000, wherein Hgb is the total hemoglobin concentration of a blood sample, and RBC is the red blood cell concentration in the blood sample, which is commonly referred to as red blood cell count. On an automated hematology analyzer, RBC and MCV are typically measured from a diluted blood sample and Hgb is measured using a lysed sample mixture as described in detail hereinafter. MCHC is derived from these directly measured parameters. Furthermore, MCHC can be obtained by cell volume measurement and an optical cell-by-cell hemoglobin measurement of hemoglobin of individual red blood cells, without lysing the cells. For the purpose of the present invention, MCHC can be obtained using either approach.

As described above, hypochromic red cell percentage (% Hypo) is defined as the percentage of red blood cells having hemoglobin concentration less than 28 g/dL. These red blood cells are detected by an optical cell-by-cell hemoglobin measurement of hemoglobin of individual red blood cells on Bayer's hematology analyzers. % Hypo has been used as an effective diagnostic criterion for detection of iron deficiency. % Hypo <5% is considered normal. Two different criteria, more specifically, % Hypo >5% and >10% have been used. % Hypo >10% has been more commonly used for defining absolute iron deficiency and functional iron deficiency (Revised European Best Practice Guidelines for the Management of Anaemia in Patients With Chronic Renal Failure, Locatelli, F. et al., *Nephrology and Dyalisis Transplantation*, Volume 19 May 2004 (Supplement 2), Appendix B, page ii39-41).

FIG. 1A illustrates the distribution of cellular or cell hemoglobin concentration (CHC) of a blood sample. As shown, the cell hemoglobin concentration of the red blood cells in a blood sample typically has a Gaussian distribution, and the mean cell hemoglobin concentration (MCHC) is at the center of the Gaussian curve. As indicated, the hypochromic red blood cells distribute in the left tail of the Gaussian curve.

Although it has been reported previously that a reduction of MCHC has been correlated with iron deficiency, however, in general MCHC has been considered insensitive to the changes in red blood cell hemoglobin content. Despite the long felt need in developing new diagnostic indicators based on those readily available hematology parameters, MCHC has not been used as a clinical diagnostic criterion for detection of iron deficiency.

As described in the Example hereinafter, in a study involving 247 clinical whole blood samples analyzed on a Coulter LH750 and a Bayer ADVIA 120 hematology analyzer, respectively, it has been found surprisingly that MCHC has a similar diagnostic ability as % Hypo for detection of iron deficiency, in other words, differentiation of the iron deficiency blood samples from the normal blood samples.

As described in the Example, a receiver operating characteristic (ROC) analysis of MCHC was performed on 247 blood samples using % Hypo $\geq$10% as the criterion for classifying normal and iron deficiency. More specifically, 105 samples having % Hypo >10% were identified as iron deficiency or positive, and 142 samples having % Hypo $\leq$10% were identified as normal or negative. The obtained ROC curve is shown in FIG. 2 and the statistic data, including AUC, standard error (SE), p-value and 95% confidence interval, are shown in Table 1.

Figure 2:
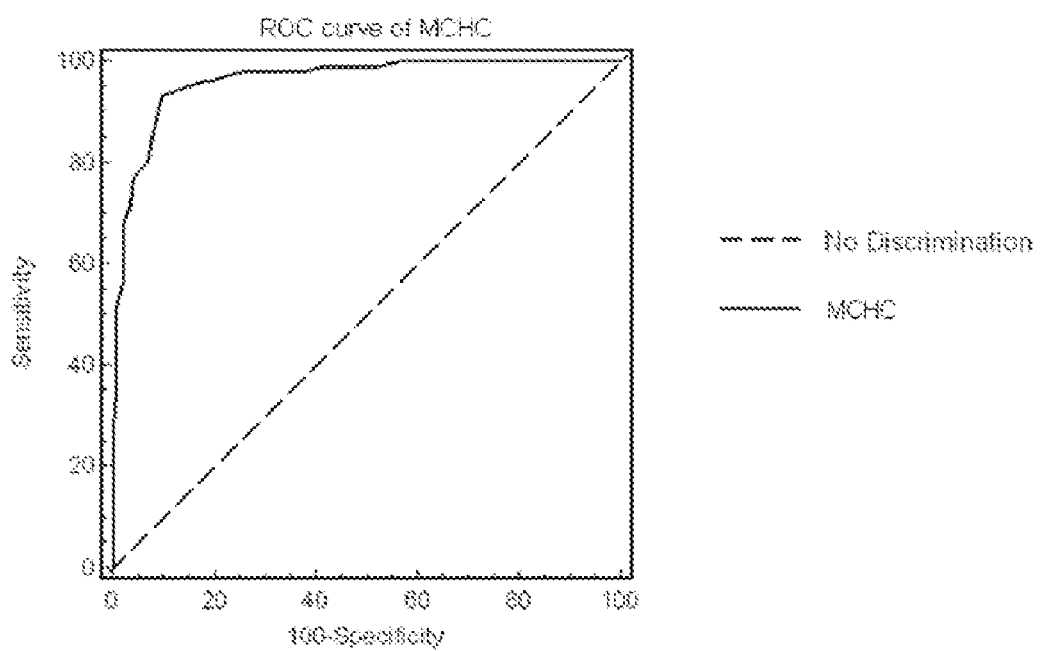
FIG. 2 is the ROC curve of MCHC, as described in the Example.

In FIG. 2, on the y-axis is plotted sensitivity (true positive fraction) and on the x-axis is plotted 100-specificity (false positive fraction). A test with perfect discrimination has an ROC curve that passes through the upper left corner, where the true-positive fraction is 100% (perfect sensitivity). The theoretical curve for a test with no discrimination is 45° diagonal line from the lower left corner to the upper right corner. The closer the curve to the upper left corner, the higher the overall accuracy of the test is. Furthermore, the area under the ROC curve (AUC) is also a common measure of the clinical accuracy of a diagnostic test. The value of AUC and ROC curve indicated that MCHC had a similar diagnostic ability as % Hypo in differentiation of the iron deficiency blood sample from the normal blood samples.

Figure 3A:
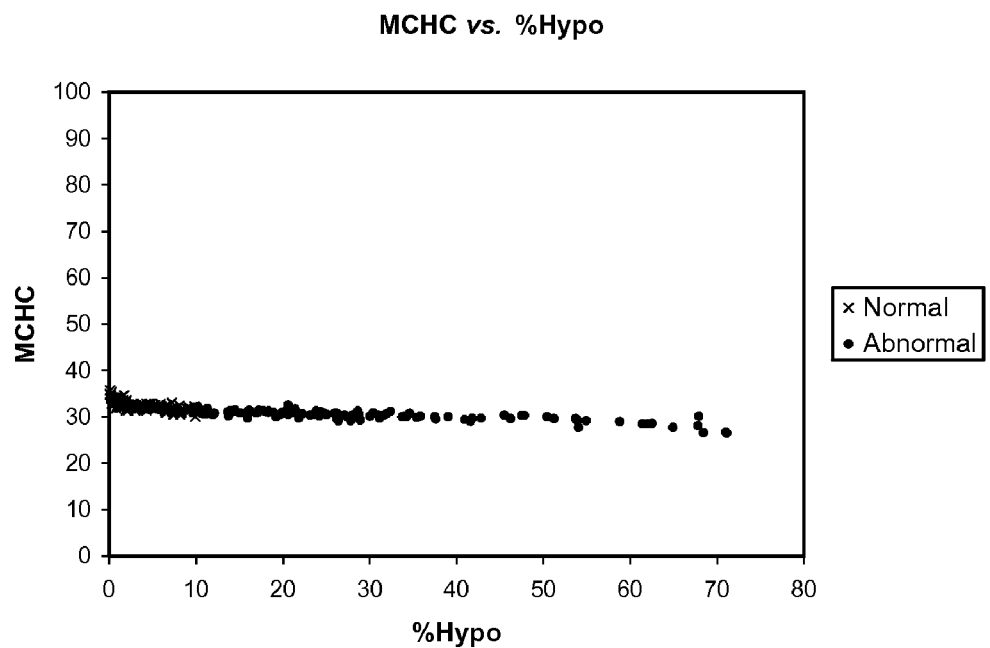
FIG. 3A shows the correlation of MCHC vs. % Hypo, as described in the Example.
Figure 3B:
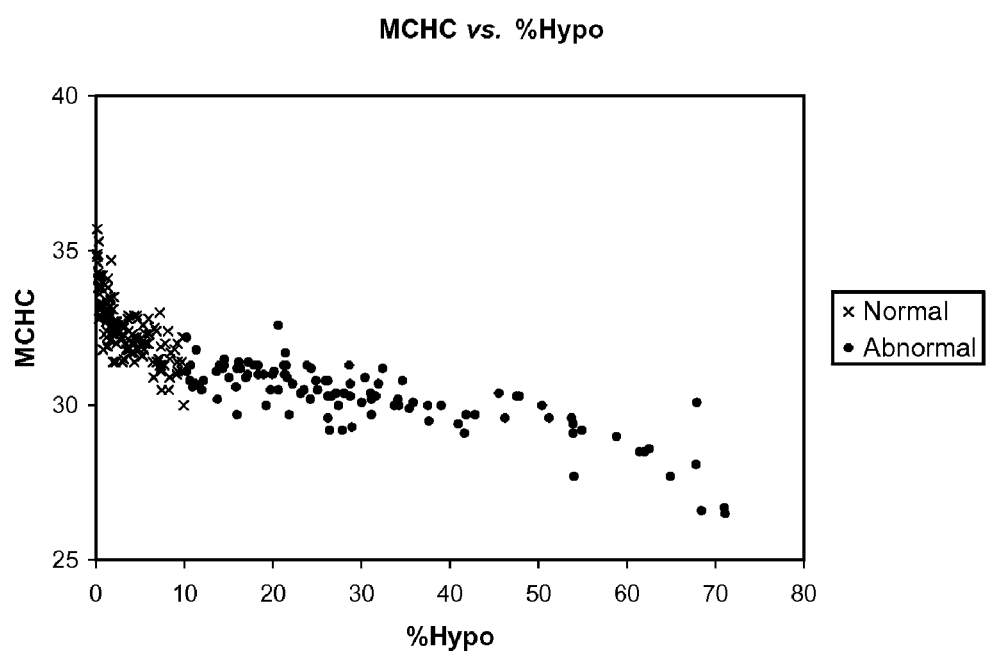
FIG. 3B shows the correlation of MCHC vs. % Hypo of FIG. 3A with an expanded scale in y-axis.

However, on the other hand, as shown in FIGS. 3A and 3B, MCHC does not have a linear correlation with % Hypo. As shown in FIG. 3B, MCHC has a non-linear, s-shape, correlation to % Hypo. As such, in the abnormal range, i.e., from 10% to about 75% of % Hypo, the MCHC value does not reflect hypochromic level of a patient or the extent of the disease. Furthermore, it can be readily appreciated that MCHC values of the normal and the abnormal blood samples vary in a fairly narrow range. As shown, these 247 blood samples have a broad % Hypo range from 0% to about 75%, while the MCHC values of these samples only vary from about 25 g/dL to about 36 g/dL. Lack of numeric resolution and linear correlation makes it difficult for clinicians to understand and to use this parameter as a diagnostic indicator.

The low hemoglobin concentration cell percentage (LHCC %) of the present invention is developed to solve the above described deficiencies of MCHC, yet maintaining the diagnostic ability of MCHC in detection of iron deficiency.

As described above, the cell hemoglobin concentration of the red blood cells in a blood sample typically has a Gaussian distribution. The left tail integral of the Gaussian curve represents the portion of the red blood cells which have low hemoglobin concentration, and this integral exhibits as an s-shape curve. It is known that a sigmoid function can transform a linear relationship to an s-shape curve, or reversely, it can also transform an s-shape curve back to a linear relationship. In one embodiment of the present invention, a sigmoid function has been utilized to simulate the relationship between MCHC and % Hypo, and to produce a function of MCHC which linearly correlates with % Hypo.

Figure 1B:
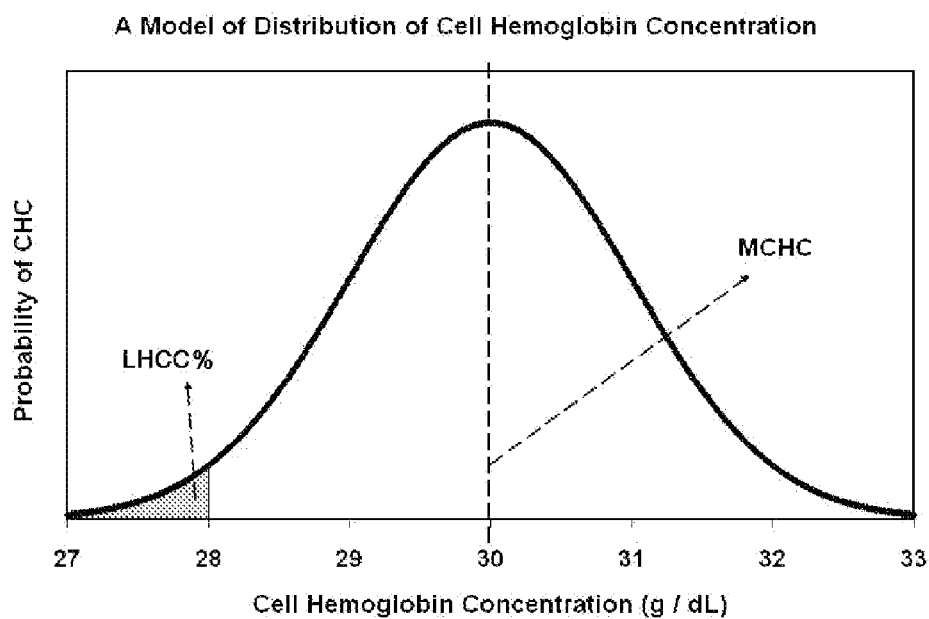
FIG. 1B is a graphic illustration of red blood cell distribution and the distribution of the low hemoglobin concentration cells represented by the sigmoid function of MCHC of the present invention.
Figure 4A:
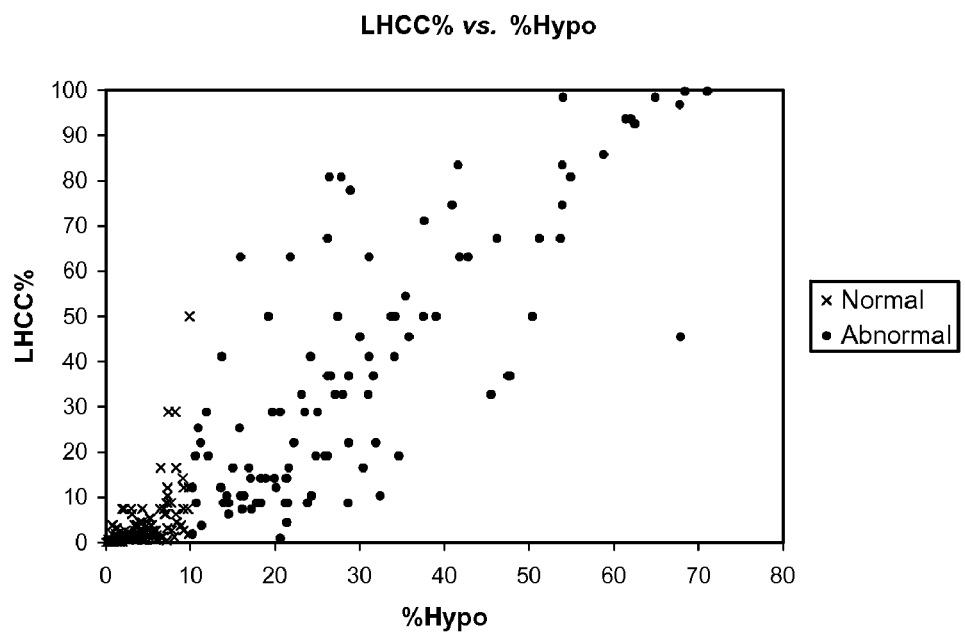
FIG. 4A shows the correlation of LHCC % vs. % Hypo, as described the Example.

FIG. 4A shows the obtained LHCC % (a sigmoid function of MCHC) versus % Hypo of these 247 clinical whole blood samples. As shown, LHCC % correlates substantially linearly with % Hypo. As such, mathematically this sigmoid function of MCHC reflects the portion of the low hemoglobin concentration cells of a blood sample, as indicated in FIG. 1B. By applying a scaling factor, this sigmoid function is expressed in percentage, hence, it is referred to as low hemoglobin concentration cell percentage (LHCC %).

It is noted that in the equation defining LHCC %, the constants d and q can vary depending on the MCHC obtained on different hematology analyzers produced by different manufacturers. It is known that MCHC obtained from different hematology analyzers vary in a certain degree depending on the detection methods and the reagents used. The d and q values described herein should not be construed as the limitation of the present invention.

The process of transforming a non-linear relationship to a linear relationship described above is mathematically referred to as a non-linear resealing. In addition to sigmoid function, other suitable mathematical functions, such as tangent and arc tangent can also be used to transform an s-shape relationship to a linear relationship, therefore, can also be used for the purpose of the present invention.

In a further embodiment, the present invention provides an enhanced LHCC % defined by the following equation:

$$\text{Enhanced } LHCC\ \% = SQRT((1-(1/(1+(EXP(d*(q-MCHC))))))) *100$$

wherein d and q are constants. In one exemplary embodiment, d and q are 1.8 and 30, respectively.

In the equation defining the enhanced LHCC %, in addition to the standard sigmoid function a square root is applied to further enhance numerical resolution in the region corresponding to the lower end of % Hypo to improve the differentiation between the normal and the abnormal among the blood samples having relatively low values of LHCC %.

Figure 4B:
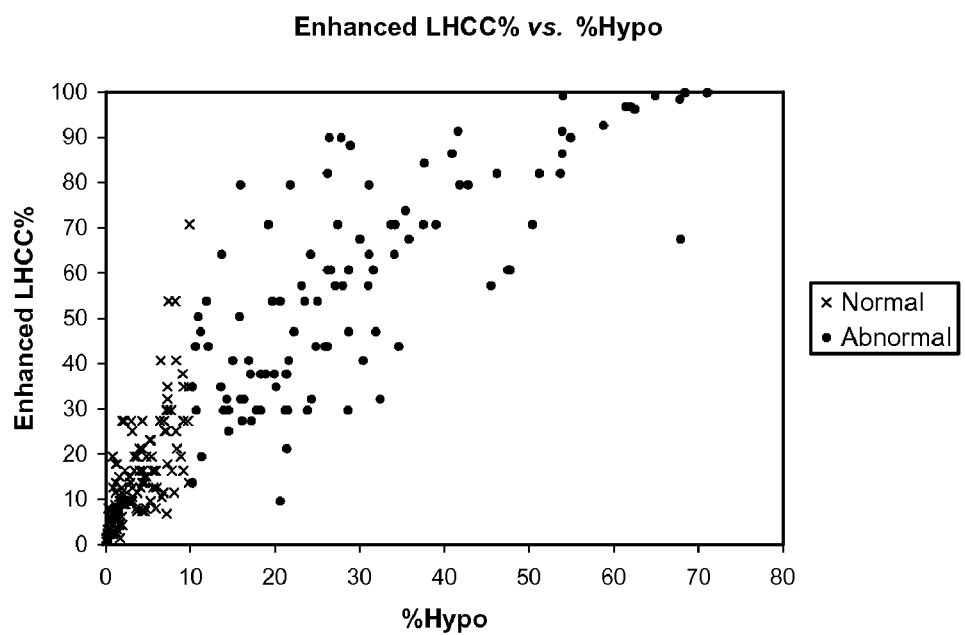
FIG. 4B shows the correlation of the enhanced LHCC % vs. % Hypo, as described in the Example.

FIG. 4B shows the enhanced LHCC % (a sigmoid function of MCHC) versus % Hypo of these 247 clinical whole blood samples. As shown, the enhanced LHCC % correlates substantially linearly with % Hypo. Furthermore, the numeric resolution in the region corresponding to the lower end of % Hypo has been increased substantially. As shown, at the lower end of the vertical axis, gradual increases of the enhanced LHCC % value can be clearly appreciated.

With regard to the method of producing LHCC % on a hematology analyzer, in one exemplary embodiment the method comprises the steps of (a) mixing a first aliquot of a blood sample with a blood diluent to form a first sample mixture, analyzing the first sample mixture on the hematology analyzer, and obtaining a mean cell volume of red blood cells (MCV) and a red blood cell concentration (RBC); (b) mixing a second aliquot of the blood sample with a reagent system to form a second sample mixture, analyzing the second sample mixture on the hematology analyzer, and obtaining a hemoglobin concentration (Hgb) of the blood sample; (c) obtaining mean cell hemoglobin concentration (MCHC) using the obtained MCV, RBC and Hgb; (d) obtaining the low hemoglobin concentration cell percentage (LHCC %) as a function of MCHC; and (e) reporting the LHCC % of the blood sample on the hematology analyzer.

In the measurement of red blood cells on a hematology analyzer a blood sample is typically diluted substantially with a diluent in a sample chamber or bath. Using an impedance measurement with a non-focused flow aperture, the blood sample can be highly diluted, for example with a dilution ratio of 6250:1. When a non-focused flow cell is used for the measurement, the dilution ratio can be substantially lower, such as 290:1. To maintain the volume and morphology of the red blood cells during their measurements on a hematology analyzer, an isotonic diluent is used for diluting the blood sample. Typically, the diluent contains one or more alkaline metal salts. Various commercially available isotonic blood diluents can be used for diluting the blood sample. Suitable examples include, but are not limited to, the diluents described in U.S. Pat. Nos. 4,521,518, 4,528,274, 5,935,857 and 6,706,526.

When a particle or a blood cell, suspended in a conductive solution, passes through a flow cell or an aperture, an electrical signal, or a pulse, can be measured due to the increase of impedance. The electrical pulses have been used for counting the number of blood cells of a blood sample. On the other hand, the pulse shape, height and width are directly related to the volume or size of a particle, and can be converted to the volume of the cell measured. When a sample that contains two or more different blood cells having different volumes is measured, a histogram obtained from the measurement can represent volume distribution of these blood cells. The detection methods and apparatus used for blood cell counting and sizing by a blood analyzer equipped with a DC impedance measurement device are generally described in U.S. Pat. Nos. 2,656,508, 3,810,011 and 5,125,737, which are hereby incorporated by reference in their entirety. Herein, the phrase "blood cell sizing" refers to the cell volume measurement.

Alternatively, low angle light scatter measurement can also be used for counting and sizing the blood cells. Herein, the term "low angle light scatter" refers to the light scatter signals measured in a range in less than 10° from the incident light.

In the cell volume measurement a cell volume distribution histogram is obtained. For the red blood cell measurement, the obtained histogram is referred to as the red blood cell distribution histogram. For a normal blood sample, a narrow and well defined red blood cell distribution, typically a Gaussian distribution, is obtained. For clinically abnormal blood samples, various distortions of the distribution have been observed, such as shift of the distribution to either higher or lower volume side, asymmetric distribution, population extension on either the higher or lower volume side, or both sides. The mean cell volume (MCV) and red blood cell distribution width (RDW) are calculated from the red blood cell distribution histogram.

The total hemoglobin concentration (Hgb) of a blood sample is typically measured on an automated hematology analyzer by mixing an aliquot of a blood sample with a lytic reagent. Upon exposing to the lytic reagent, the red blood cells are completely lysed, and hemoglobin is released to the sample mixture, which upon reacting with a ligand in the lytic reagent forms a chromogen. The hemoglobin chromogen is then measured by UV-VIS spectroscopy at a predetermined wavelength, and Hgb is calculated from the measurement. One lysing reagent system suitable for measuring Hgb comprises an isotonic blood diluent, such as the diluents described in U.S. Pat. Nos. 4,521,518, 4,528,274, 5,935,857 and 6,706,526, and a lysing reagent, such as the lysing reagents described in U.S. Pat. Nos. 5,763,280, 5,834,315 and 6,573,102, these are hereby incorporated by reference in their entirety. Alternatively, the reagent system can also be a single lysing reagent as described in U.S. Pat. No. 5,882,934 which is hereby incorporated by reference in its entirety. Furthermore, various lytic reagents known in the art for measurement of hemoglobin can be used for the purpose of the present invention.

On the Coulter LH750 or GEN*S hematology analyzer (Beckman Coulter, Inc. Fullerton, Calif.), several aliquots of a blood sample are analyzed concurrently in different analysis modes. In the CBC mode, a first aliquot of a blood sample is diluted by a diluent to form a first sample mixture, and red blood cells and platelets are measured from the first sample mixture. At the same time, a second aliquot of the blood sample is mixed with a diluent and a lytic reagent to form a second sample mixture, and the hemoglobin concentration is measured using the second sample mixture. Various red blood cell parameters, among others, are reported from these measurements, which include red blood cell concentration (RBC), mean cell volume (MCV), total hemoglobin concentration (Hgb), mean cell hemoglobin (MCH), mean cell hemoglobin concentration (MCHC), and etc. On these hematology analyzers, MCHC is calculated from MCV, RBC and Hgb.

In a further aspect, the present invention provides a method for detection of iron deficiency using LHCC % or the enhanced LHCC % defined above.

More specifically, the method comprises the following steps: (a) analyzing a blood sample on a hematology analyzer and obtaining MCHC of the blood sample; (b) obtaining LHCC %, or the enhanced LHCC % using the obtained MCHC; (c) comparing the LHCC % or the enhanced LHCC % to a predetermined iron deficiency criterion; and (d) reporting an indication of iron deficiency if the LHCC %, or the enhanced LHCC % meets the predetermined iron deficiency criterion.

It is noted that the predetermined iron deficiency criterion described herein, is also commonly referred to as the cut-off value for diagnosis of the clinical condition, as used in the example described hereinafter. For example, the predetermined iron deficiency criterion defines iron deficiency if LHCC % is greater than the cut-off value for LHCC %. As such, the predetermined iron deficiency criterion is specific to each function, for example, it can be referred to as a predetermined LHCC % iron deficiency criterion or a predetermined enhanced LHCC % iron deficiency criterion.

The Example further illustrates the method of the present invention using LHCC % and enhanced LHCC % defined above for detection of iron deficiency in comparison to % Hypo. In the study, LHCC % and the enhanced LHCC % values of 247 clinical whole blood samples were calculated using the MCHC reported from the Coulter LH750 hematology analyzer, wherein LHCC % was defined by the equation of LHCC %=1/(1+(EXP(1.8*(30−MCHC))))*100; and the enhanced LHCC % was defined by the equation of LHCC % =SQRT((1−(1/(1+(EXP(1.8*(30−MCHC))))))) *100.

As illustrated in FIGS. 4A and 4B, the obtained LHCC % and the enhanced LHCC % values distribute between 0 and 100%, in a comparable range of % Hypo, and correlate substantially linearly with % Hypo.

As shown in FIG. 4B, the majority of the normal blood samples have the enhanced LHCC % values from 0 to about 27%, and the majority of the iron deficiency samples have the enhanced LHCC % values in a broad range from about 27% to 100%. With the improved numeric resolution, it is convenient for the clinicians to recognize the iron deficiency samples. As can be appreciated, because of its substantially linear correlation with the percentage of hypochromic cells, and broad distribution range for the iron deficiency samples, this index may potentially reflect hypochromic level of a patient and may be utilized to assist in determining severity of hypochromia.

Figure 5A:
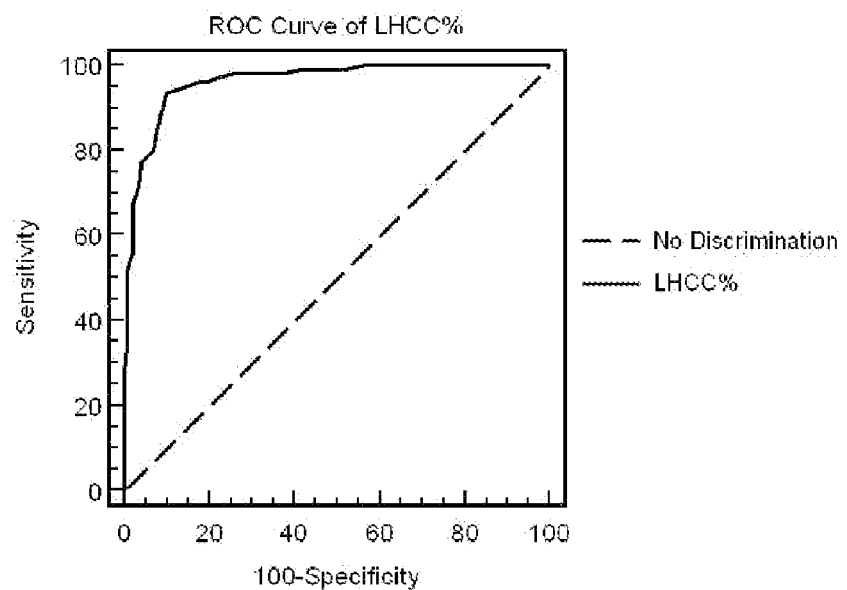
FIG. 5A is the ROC curve of LHCC %, as described in the Example.
Figure 5B:
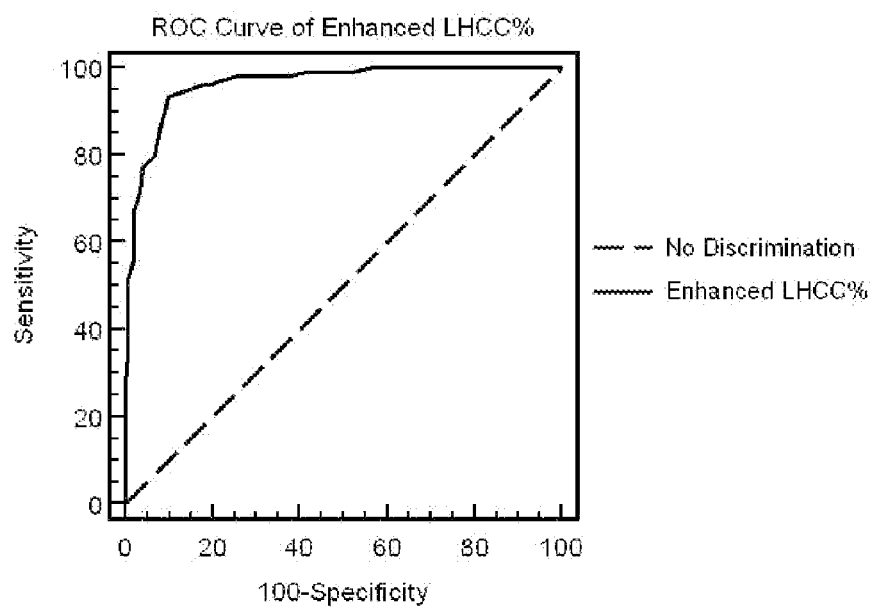
FIG. 5B is the ROC curve of enhanced LHCC %, as described in the Example.

The clinical accuracy of LHCC % and the enhanced LHCC % for detection of iron deficiency is evaluated using the ROC analysis of these 247 clinical whole blood samples as described in the Example. FIGS. 5A and 5B show the ROC curves of LHCC % and the enhanced LHCC %, respectively. Table 1 shows the statistic analysis results of the ROC analysis of LHCC %. As shown, AUC is 0.962 for LHCC %, which indicates that LHCC % correlates highly with % Hypo. The value of AUC and ROC curve indicate that LHCC % has a similar diagnostic ability as % Hypo in detection of iron deficiency. With a cut-off of 7.45, LHCC % has a sensitivity of 93.3% and a specificity of 90.1%.

As shown in FIG. 5B, the ROC curve for the enhanced LHCC % is the same as that of LHCC %. The statistic analysis results of the ROC analysis of the enhanced LHCC % are the same as those obtained for LHCC % shown in Table 1. With a cut-off of 27.3%, the enhanced LHCC % has a sensitivity of 93.3% and a specificity of 90.1%. This means that both LHCC % and the enhanced LHCC % have the same clinical accuracy for detection of iron deficiency, and both have a similar diagnostic ability as % Hypo in detection of iron deficiency.

As can be appreciated from the above, both LHCC % and the enhanced LHCC % have improved the diagnostic ability of MCHC, because both LHCC % and the enhanced LHCC % can linearly represent the percentage of the low hemoglobin concentration cells of a blood sample.

Furthermore, as described above, as shown in FIG. 4B at the lower end of the vertical axis, gradual increases of the enhanced LHCC % value can be clearly appreciated. This further improves the sensitivity of this diagnostic indicator for identifying sub-abnormal conditions, such as those blood samples having increased low hemoglobin concentration cells, yet still in a pre-anemic stage.

As such, LHCC % or the enhanced LHCC % of the present invention can be used as an effective indicator for detection of iron deficiency. Its substantially improved numeric resolution provides feasibility for a clinical diagnostic tool. Moreover, its substantial linear correlation to % Hypo can potentially be utilized for quantitative assessment of hypochromic condition.

As described above, % Hypo must be measured using a fresh whole blood sample in less than 4 hours after blood collection, because sample aging leads to erroneous increases of % Hypo report due to red blood cell swelling. On the contrary, MCHC is stable at 24 hours after blood collection. As such, for the purpose of diagnosis of iron deficiency LHCC % can be obtained using a routine hematology analysis of the whole blood sample, without being restricted by the narrow window of sample age as that required in the analysis of % Hypo. This provides a substantial advantage for the hematology laboratories in terms of sample handling and work flow management. For example, in various commercial hematology laboratories, many whole blood samples are collected in individual doctor's offices and sent to the laboratories for analysis. The blood samples are often received 24 hours or more after blood collection. These samples are no longer suitable for the analysis of % Hypo. However, reliable LHCC % can still be obtained with these 24 hour old samples.

It should be understood that the reported Hgb, MCV and RBC vary slightly among different hematology analyzers depending on the detection methods and the reagents used by different instrument manufacturers. Consequently, MCHC, the derived parameter, varies by a certain degree among different hematology analyzers. Therefore, the cut-off value, or the corresponding predetermined iron deficiency criterion for LHCC % or the enhanced LHCC % in the method of the present invention can vary depending on the hematology analyzers used. Furthermore, it is known that Hgb, MCV and RBC, and the derived MCHC can vary depending on the patient demographics, as well as clinical focus of a particular hospital or facility, such as a cancer center or kidney dialysis center. As such, the cut-off value for LHCC % or the enhanced LHCC % for the purpose of the present invention should be confirmed empirically for each hospital or the hematology analyzer used. The cut-off values for LHCC % or the enhanced LHCC % obtained in the study shown herein exemplify the utility of the method of the present invention, and should not be construed as limitations of the present invention.

It can be appreciated MCHC is a reported parameter on all commercial hematology analyzers produced by all manufacturers, including both high through-put instruments and the small instruments used in the doctor's office. Therefore, LHCC % or the enhanced LHCC %, the indexes required for detection of iron deficiency using the method of the present invention, can be obtained from all commercial hematology analyzers.

Furthermore, the method of the present invention using LHCC % or the enhanced LHCC % for detection of iron deficiency is a time saving and low cost approach, because these parameters can be obtained from a routine hematology analysis of a whole blood sample without additional cost.

The following examples are illustrative of the invention and are in no way to be interpreted as limiting the scope of the invention, as defined in the claims. It will be understood that various other ingredients and proportions may be employed, in accordance with the proceeding disclosure.

EXAMPLE 247 clinical whole blood samples were analyzed on a Coulter LH750 and a Bayer ADVIA 120 hematology analyzer, respectively, at University College Hospital of London. All hematology analyzers were operated under their standard operating conditions, and calibrated using the calibration materials provided by the manufacturers according to the operator manual and the protocol of the study.

On the Coulter LH750 hematology analyzer (Beckman Coulter, Inc., Fullerton, Calif.), the sample was analyzed using the CBC and Retic modes. A first aliquot of 1.6 µl of a blood sample was diluted by Isoton 3E with a dilution ratio of 6250:1, to form a first sample mixture, which was measured by the DC impedance measurements to produce the red blood cell parameters. A second aliquot of 28 µl of the blood sample was diluted with 6 ml of Isoton 3E, and then mixed with 1 ml of Lyse S III diff to form a second sample mixture. The absorption of the second sample mixture was measured at about 540 nm to obtain Hgb. All reagents described above were the products of Beckman Coulter, Inc.

MCHC of each blood samples was obtained on the Coulter LH750 hematology analyzer. The correlation of MCHC vs. % Hypo was shown in FIG. 3A and in FIG. 3B in an expanded scale. As shown, MCHC has a non-linear correlation with % Hypo.

A receiver operating characteristic (ROC) analysis was performed on MCHC obtained on the Coulter LH750 hematology analyzer, using % Hypo >10% as the criterion for classifying normal and iron deficiency. More specifically, 105 samples having % Hypo >10% were identified as iron deficiency or positive, and 142 samples having % Hypo ≦10% were identified as normal or negative. The obtained ROC curve is shown in FIG. 2 and the statistic data, including AUC, standard error (SE), p-value and 95% confidence interval, are shown in Table 1. The value of AUC and ROC curve indicated that MCHC had a similar diagnostic ability as % Hypo in detection of iron deficiency.

LHCC % and the enhanced LHCC % were calculated using the MCHC reported from the Coulter LH750 hematology analyzer, wherein LHCC % was defined by the equation of LHCC %=$1/(1+(EXP(1.8*(30-MCHC))))*100$; and the enhanced LHCC % was defined by the equation of Enhanced LHCC %=$SQRT((1-(1/(1+(EXP(1.8*(30-MCHC))))))*100$ FIGS. 4A and 4B showed the obtained LHCC % vs. % Hypo, and the enhanced LHCC % vs. % Hypo, respectively. As shown, both LHCC % and the enhanced LHCC % had a substantially linear correlation with % Hypo. A linear regression analysis was performed between LHCC % and % Hypo, and between the enhanced LHCC % and % Hypo. The obtained correlation coefficients (r) were 0.8938, and 0.8950, respectively.

A receiver operating characteristic (ROC) analysis was performed on LHCC % and the enhanced LHCC % using % Hypo >10% as the criterion as described above. The obtained ROC curves were shown in FIGS. 5A and 5B. The statistic data, including AUC, standard error (SE), p-value and 95% confidence interval are the same for both LHCC % and the enhanced LHCC %, and are shown in Table 1.

As shown, LHCC % and the enhanced LHCC % correlated highly with % Hypo. The value of AUC and ROC curves indicated that LHCC % and the enhanced LHCC % had a similar diagnostic ability as % Hypo in detection of iron deficiency. The cut-off values for LHCC % and the enhanced LHCC % were obtained from the ROC analysis.

With a cut-off equal to 7.45, LHCC % had a sensitivity of 93.3% and a specificity of 90.1%. With a cut-off equal to 27.3%, the enhanced LHCC % had a sensitivity of 93.3% and a specificity of 90.1%.

TABLE 1

Statistic Data of ROC Analysis of MCHC and LHCC % (% Hypo >10%)

| Statistics | MCHC | LHCC % |
|---|---|---|
| AUC | 0.962 | 0.962 |
| SE | 0.012 | 0.013 |
| P-value | <0.0001 | <0.0001 |
| Lower | 0.93 | 0.93 |
| Upper | 0.982 | 0.982 |

The invention has been described with reference to particularly preferred embodiments. It will be appreciated, however, that various changes can be made without departing from the spirit of the invention, and such changes are intended to fall within the scope of the appended claims. While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents. All patents and other publications cited herein are expressly incorporated by reference.

What is claimed is:

1. A method of producing a low hemoglobin concentration cell percentage (LHCC %) of a blood sample on a hematology analyzer comprising:
   (a) mixing a first aliquot of a blood sample with a blood diluent to form a first sample mixture, analyzing said first sample mixture on said hematology analyzer, and obtaining a mean cell volume of red blood cells (MCV) and a red blood cell concentration (RBC);
   (b) mixing a second aliquot of said blood sample with a reagent system to form a second sample mixture, analyzing said second sample mixture on said hematology analyzer, and obtaining a hemoglobin concentration (Hgb) of said blood sample;
   (c) obtaining mean cell hemoglobin concentration (MCHC) using said MCV, said RBC and said Hgb;
   (d) obtaining said low hemoglobin concentration cell percentage (LHCC %) defined as a function of said MCHC obtained by non-linear rescaling of said MCHC; and
   (e) reporting said LHCC % of said blood sample on said hematology analyzer.

2. The method of claim 1, wherein said LHCC % is a sigmoid function of said MCHC.

3. The method of claim 1, wherein said LHCC % is defined by following equation:

$$LHCC\% = 1/(1+(EXP(d*(q+MCHC))))*100$$

wherein d and q are constants.

4. The method of claim 3, wherein said d and q are 1.8 and 30, respectively.

5. The method of claim 1, wherein said LHCC % is an enhanced LHCC % defined by following equation:

$$\text{Enhanced } LHCC\% = SQRT((1-(1/(1+(EXP(d*(q-MCHC))))))))*100$$

wherein d and q are constants.

6. The method of claim 5, wherein said d and q are 1.8 and 30, respectively.

7. The method of claim 1, wherein said low hemoglobin concentration cell percentage (LHCC %) correlates linearly with hypochromic red cell percentage.

8. A method of detection of iron deficiency comprising the steps of:
   (a) analyzing a blood sample on a hematology analyzer and obtaining mean cell hemoglobin concentration (MCHC) of red blood cells;
   (b) obtaining a low hemoglobin concentration cell percentage (LHCC %) defined as a function of said MCHC obtained by non-linear rescaling of said MCHC;
   (c) comparing said LHCC % to a predetermined iron deficiency criterion; and
   (d) reporting an indication of iron deficiency if said LHCC % meets said predetermined iron deficiency criterion.

9. The method of claim 8, wherein said LHCC % is a sigmoid function of said MCHC.

10. The method of claim 8, wherein said LHCC % is defined by following equation:

$$LHCC\% = 1/(1+(EXP(d*(q-MCHC))))*100$$

wherein d and q are constants.

11. The method of claim 10, wherein said d and q are 1.8 and 30, respectively.

12. The method of claim 8, wherein said LHCC % is an enhanced LHCC % defined by following equation:

$$\text{Enhanced } LHCC\% = SQRT((1-(1/(1+(EXP(d*(q-MCHC))))))))*100$$

wherein d and q are constants.

13. The method of claim 12, wherein said d and q are 1.8 and 30, respectively.

* * * * *